United States Patent [19]

Simon et al.

[11] Patent Number: 5,773,430
[45] Date of Patent: Jun. 30, 1998

[54] SERINE PROTEINASE INHIBITORY ACTIVITY BY HYDROPHOBIC TETRACYCLINE

[75] Inventors: Sanford R. Simon, Stony Brook; Elizabeth J. Roemer, Port Jefferson; Lorne M. Golub; Nungavaram S. Ramamurthy, both of Smithtown, all of N.Y.

[73] Assignee: Research Foundation of State University of New York, Albany, N.Y.

[21] Appl. No.: 816,551

[22] Filed: Mar. 13, 1997

[51] Int. Cl.$^6$ .................................................. A61K 31/65
[52] U.S. Cl. .......................................................... 514/152
[58] Field of Search ............................................. 514/152

[56] References Cited

U.S. PATENT DOCUMENTS

| Re. 34,656 | 7/1994 | Golub et al. | 514/152 |
|---|---|---|---|
| 4,666,897 | 5/1987 | Golub et al. | 514/152 |
| 4,704,383 | 11/1987 | McNamara et al. | 514/152 |
| 4,935,411 | 6/1990 | McNamara et al. | 514/152 |
| 4,935,412 | 6/1990 | McNamara et al. | 514/152 |
| 5,045,538 | 9/1991 | Schneider et al. | 514/152 |
| 5,223,248 | 6/1993 | McNamara et al. | 514/152 |
| 5,258,371 | 11/1993 | Golub et al. | 514/152 |
| 5,308,839 | 5/1994 | Golub et al. | 514/152 |
| 5,321,017 | 6/1994 | Golub et al. | 514/152 |
| 5,459,135 | 10/1995 | Golub et al. | 514/152 |
| 5,523,297 | 6/1996 | Pruzanski et al. | 514/152 |
| 5,532,227 | 7/1996 | Golub et al. | 514/152 |

OTHER PUBLICATIONS

Simon et al., "Inhibition of Human Neutrophil Elastase by Polyguanylic Acid and Other Synthetic Polynucleotides", Adv. Exp. Med. Biol., 240, 65–74 (1988).
Tyagi et al., "Inhibitors Directed to Binding Domains in Neutrophil Elastase", Biochemistry, 20, 9970–9977 (1990).
Tyagi et al. "Parinaric Acids As Probes of Binding Domains in Neutrophil Elastase ", J. Biol. Chem. 266, 15185–15191 (1991).
Tyagi et al., "Interaction of Neutrophil Elastase With Hydrophobic Polyanionic Chelators", Biochem. Cell. Biol., 69, 624–629 (1991).
Bode et al., "Human Leukocyte and Porcine Pancreatic Elastase: X–Ray Crystal Structures, Mechanism, Substrate Specificity and Mechanism–Based Inhibitors", 28, 1951–1963 (1989).
Yu et al., "Chemically Modified Tetracycline Normalizes Collagen Metabolism in Diabetic Rats", J. Periodontol. Res., 28, 420–428 (1993).
Ramamurthy et al., "Diabetes Increases Collagenase Activity in Extracts of Rat Gingiva and Skin", J. Periodontol. Res., 18, 23–30 (1983).
Roemer et al., "In Vitro Assay Systems for Inflammatory Cell–Mediated Damage to Interstitial Extracellular Matrix", In Vitro Toxicology, 7, 75–81 (1994).
Roemer et al., "In Vitro Assay Systems for Cell Interactions with Interstitial Extracellular Matrix", In Vitro Technology, 7, 209–224 (1994).
Golub et al., "Further Evidence that Tetracyclines Inhibit Collagenase Activity in Human Crevicular Fluid and From Other Mammalian Sources", Journal of Periodontal Research, 20, 12–23 (1985).
Sorsa et al., "Doxycycline in the Protection of Serum Alpha–1–Antitrypsin from Human Neutrophil Collagenase and Gelatinase ", Antimicrobial Agents and Chemotherapy, 37, 592–594 (1993).
Golub et al., "Treating Periodontal Diseases by Blocking Tissue–Destructive Enzymes", JADA, 125, 163–171 (1994).
Mallya et al., "Interaction of Matrix Metalloproteinases with Serine Protease Inhibitors", Annals of the New York Academy of Sciences, 732, 303–314 (1994).
Simon, "Oxidants, Metalloproteases and Serine Proteases in Inflammation", Protease, Protease Inhibitors and Protease–Derived Peptides, 27–37 (1993).
Ying et al., "Inhibition of Human Leucocyte Elastase by Ursolic Acid", Biochem. J., 277, 521–526 (1991).
Cunningham et al., "Synthesis and Evaluation of CE–0266: A New Human Neutrophil Elastase Inhibitor", Bioorganic Chemistry, 20, 345–355 (1992).
Kirschenheuter et al., "Synthesis and Characterization of Human Neutrophil Elastase Inhibitors Derived from Aromatic Esters of Phenylalkanoic Acids", Proteases, Protease Inhibitors and Protease–Derived Peptides, 71–82 (1993).
Chang et al., "Local and Systemic Factors in Periodontal Disease Increase Matrix–Degrading Enzyme Activities in Rat Gingiva: Effect of Minocycline Therapy", Research Communication in Molecular Pathology and Pharmacology, 91, 303–318 (1996).
Ryan et al., "Matrix Metalloproteinases and Their Inhibition in Periodontal Treatment", Current Opinion in Periodontology, 3, 85–96 (1996).
Golub et al., "Tetracyclines Inhibit Connective Tissue Breakdown: New Therapeutic Implications for an Old Family of Drugs", Critical Reviews in Oral Biology and Medicine, 2, 297–322 (1991).
Rinehart et al., "Human $\alpha_1$–Proteinase Inhibitor Binds to Extracellular Matrix In Vitro", Am. J. Respir. Cell Mol. Biol., 9, 666–679 (1993).
Mitscher, "Chemical Transformations of the Tetracycline Family", The Chemistry of Tetracyclines, 165–218 (1978).

*Primary Examiner*—Kevin E. Weddington
*Attorney, Agent, or Firm*—Hoffmann & Baron, LLP

[57] ABSTRACT

A method for inhibiting the activity of serine proteinase in biological systems includes administering to the system a serine proteinase inhibitory amount of a hydrophobic 4-de (dimethylamino)tetracycline. The method reduces tissue destruction during inflammation resulting from the activity of human leukocyte elastase. The method is used for pharmaceutical and cosmetic purposes.

18 Claims, 8 Drawing Sheets

FIG-1 CMT + PMN (0.5 nM PMA) + ECH (3H-Pro) (4h at 37 C - avg of 4 expts)

FIG-3A  THE INHIBITORY EFFECTS OF CMT-3 ON HLE (DIXON PLOT)

FIG-3B THE INHIBITORY EFFECTS OF CMT-3 ON HLE (CORNISH-BOWDEN PLOT)

FIG-4B THE INHIBITORY EFFECTS OF CMT-3 ON HLE (CORNISH-BOWDEN PLOT)

FIG-5  THE EFFECTS OF DOXYCYCLINE ON HLE (DIXON PLOT)

SERINE PROTEINASE INHIBITORY ACTIVITY BY HYDROPHOBIC TETRACYCLINE

This invention was made with Government support under DE 10985 and R37-DE03987 awarded by the National Institute of Dental Research (NIH). The Government has certain rights in the invention.

BACKGROUND OF THE INVENTION

1. Field of the Invention

The invention relates to a method of using hydrophobic tetracycline for the inhibition of serine proteinase activity in biological systems. The invention more particularly relates to a therapeutic use of a 4-de(dimethylamino)tetracycline to treat mammals suffering from inflammation-mediated tissue destruction resulting from activity of serine proteinase leukocyte elastase.

2. Description of the Related Art

Damage to connective tissues is a major complication of the inflammatory response. Such inflammatory tissue injury contributes, for example, to the pathological changes to the joints in the arthritides, to the lungs in emphysema and in respiratory distress syndrome, to the kidneys and the digestive tract in syndrome of multiple organ failure, to the gingiva and periodontium in periodontitis, and to the heart and brain in ischemia-reperfusion syndrome. Proteases released by leukocytes play a major role in tissue injury associated with inflammatory response.

Two classes of proteases have been linked to inflammatory tissue injury: serine proteinases and matrix metalloproteinases (MMP's). Serine proteinases have a substrate specificity and mode of substrate binding differing entirely from the substrate specificity and mode of substrate binding of the MMP's.

Serine proteinases have been classified by their substrate specificity into three types: trypsin-like, chymotrypsin-like and elastase-like. Serine proteinase elastase prefers substrates with small aliphatic chains (e.g., Ala, Val) in the $P_1$ position. $P_1$, $P_2$, etc. are groups on the natural substrate of a protease that flank the cleavage site of the substrate and are presumed to fit subsites on the enzyme, usually designated $S_1$, $S_2$, etc. The mode of action of serine proteinases involves the amino acid serine which has a hydroxyl group that acts as a nucleophile for hydrolytic cleavage. In contrast, in matrix metalloproteinases, a metal, which is usually zinc, coordinates and activates the target protein amide carbonyl for hydrolysis. Therefore, serine proteinase elastase differs from MMP elastase.

Considerable energy has been devoted to developing inhibitors of serine proteinase elastase (human leukocyte elastase or HLE), especially because of its putative role in the mechanism of lung injury associated with emphysema and respiratory distress syndrome.

Inhibition of human leukocyte elastase by non-peptidic natural products, exemplified by pentacyclic triterpenoides of plant origin, particularly ursolic acid, is described by Q-L Ying et al., "Inhibition of Human Leucocyte Elastase by Ursolic Acid: Evidence for a Binding Site for Pentacyclic Triterpenes", *Biochem. J* 277, 521–526 (1991).

Other nonpeptidic human leukocyte elastase inhibitors of synthetic origin such as 4-(methylsulfinyl) phenyl 2-1-(1-methyl-2-pyrrolyl) butyrate and related sulfide and sulfone derivatives, are described by R. T. Cunningham, et al., "Synthesis and Evaluation of CE-0266: A New Human Neutrophil Elastase Inhibitor", *Bioorganic Chemistry*, 20, 345–355 (1992). Additional analogs of these compounds which are HLE inhibitors are described by G. P. Kirschenheuter et al., "Synthesis and Characterization of Human Neutrophil Elastase Inhibitors Derived From Aromatic Esters of Phenylalkanoic Acids", in Proteases, *Protease Inhibitors and Protease— Derived Peptides*, Birkhäuser Verlag, Basel (1993), pp 71–82. These non-peptide compounds of natural or synthetic origin are low molecular weight, hydrophobic, anionic inhibitors.

It is believed that low molecular weight inhibitors of HLE preferably have an extended hydrophobic domain, with a center of negative charge. Analysis of the three-dimensional binding site of leukocyte elastase by X-crystallography indicates that the extended substrate binding site for this enzyme is largely lined by hydrophobic residues, but an arginine side chain (not directly part of the catalytic triad) in the midst of this hydrophobic milieu contributes structurally to stabilizing the structure of the active site. It is presumed that both peptide- and non peptide-based hydrophobic, anionic compounds which can serve as inhibitors bind to the extended substrate binding site through a combination of hydrophobic forces and electrostatic interactions with the arginine residue.

Other examples of nonpeptidic, hydrophobic-anionic inhibitors of HLE are fatty acids, bile acids, and pyrene trisulfonic acid, all of which have also been investigated in the laboratory of one of the inventors herein. S. Simon, et al., "Inhibition of Human Neutrophil Elastase by Polyguanylic Acid and Other Synthetic Polynucleotides," *Adv. Exp. Med Biol.* 240, 65–74 (1988); S. C. Tyagi and S. R. Simon, "Inhibitors Directed to Binding Domains in Neutrophil Elastase," *Biochemistry* 20, 9970–9977 (1990); S. Tyagi and S. R. Simon, "Parinaric Acids as Probes of Binding Domains in Neutrophil Elastase," *J. Biol. Chem.* 266, 15185–15191 (1991); S. Tyagi and S. R. Simon, "Interaction of Neutrophil Elastase With Hydrophobic Polyanoinic Chelators," *Biochem. Cell Biol* 69, 624–629 (1991). These compounds are all reversible inhibitors, and form no covalent interactions with the enzyme. Because they bind at the extended substrate binding site, they are competitive inhibitors of enzymatic hydrolysis of larger oligopeptide substrates and proteins such as elastin, but are noncompetitive inhibitors of hydrolysis of the smallest synthetic substrates which bind only in the immediate vicinity of the catalytic triad within the active site.

None of these nonpeptide compounds of natural or synthetic origin resembles tetracycline.

Tetracyclines are a class of compounds which are particularly well known for their early and spectacular success as antibiotics. Such compounds as tetracycline, sporocycline, etc., are broad spectrum antibiotics, having utility against a wide variety of bacteria and other microbes. The parent compound, tetracycline, has the following general structure:

The numbering system of the multiple ring nucleus is as follows:

Tetracycline, as well as the 5-OH (oxytetracycline, e.g., terramycin™) and 7-Cl (chlorotetracycline, e.g., aureomycin™) derivatives, exist in nature, and are all well known antibiotics. Semisynthetic tetracyclines include, for example, doxycline, minocycline and methacycline. The use of tetracycline antibiotics, while generally effective for treating infection, can lead to undesirable side effects. For example, the long-term administration of antibiotic tetracyclines can reduce or eliminate healthy flora, such as intestinal flora, and can lead to the production of antibiotic resistant organisms or the overgrowth of yeast and fungi. These significant disadvantages typically preclude treatment regimens requiring chronic administration of these compounds.

Natural tetracyclines may be modified without losing their antibiotic properties, although certain elements of the structure must be retained to do so. A class of compounds has been defined which are structurally related to the antibiotic tetracyclines, but which have had their antibiotic activity substantially or completely extinguished by chemical modification. The modifications that may and may not be made to the basic tetracycline structure were reviewed by Mitscher, L. A., *The Chemistry of the Tetracycline Antibiotics*, Marcel Dekker, New York (1978), Ch. 6. According to Mitscher, the modification at positions 5–9 of the tetracycline ring system can be made without causing the complete loss of antibiotic properties. However, changes to the basic structure of the ring system, or replacement of substituents at positions 1–4 or 10–12, generally lead to synthetic tetracyclines with substantially less, or essentially no, antibacterial activity.

Chemically modified tetracyclines (CMT's) include, for example, 4-de(dimethylamino)tetracycline (CMT-1), tetracyclinonitrile (CMT-2), 6-demethyl-6-deoxy-4-de(dimethylamino)tetracycline (CMT-3), 7-chloro-4-de(dimethylamino)tetracycline (CMT-4), tetracycline pyrazole (CMT-5), 4-hydroxy-4-de(dimethylamino)tetracycline (CMT-6), 4-de(dimethylamino)-12α-deoxytetracycline (CMT-7), 6-deoxy-5α-hydroxy-4-de(dimethylamino) tetracycline (CMT-8), 4-de(dimethylamino)-12α-deoxyanhydrotetracycline (CMT-9), 4-de(dimethylamino) minocycline (CMT-10).

Further examples of tetracyclines modified for reduced antimicrobial activity include the 4-epimers of oxytetracycline and chlorotetracycline (epi-oxytetracycline and epi-chlorotetracycline).

Certain tetracyclines have been shown to suppress matrix metalloproteinases, and the laboratories of two of the inventors herein have played a major role in identifying tetracyclines as a family of compounds which can inhibit MMP's independently of tetracycline antibiotic activity. U.S. Pat. Nos. 5,459,135 to Golub et al., 5,321,017 to Golub et al., 5,308,839 to Golub et al., 4,935,412 to McNamara et al., 4,704,383 to McNamara et al., and 4,666,897 to Golub et al. describe the use of non-antimicrobial tetracyclines to treat tissue-destructive conditions, chronic inflammation and other conditions associated with excess metalloprotease activity of matrix metalloproteinases such as collagenase, gelatinase and MMP elastase.

Inhibition of matrix metalloproteinase activity by tetracyclines is shown in a series of studies involving experimental animals in which periodontitis is iatrogenically induced by infection with oral pathogens or in which periodontal ligament atrophy is induced by destruction of pancreatic islets, resulting in pathological elevation of MMP activity at the sites of tissue injury. Treatment of these animals with semisynthetic tetracyclines which retain antibiotic activity as well as chemically modified tetracyclines devoid of any antibiotic activity results in marked reduction in MMP levels at the sites of tissue injury as well as marked improvement of the periodontium in the animals. See, e.g., K. M. Chang et al., "Local and Systemic Factors in Periodontal Disease Increase Matrix-Degrading Enzyme Activities in Rat Gingiva: Effect of Minocycline Therapy", *Research Communications in Molecular Pathology and Pharmacology*, 91, 303–318 (1996); M. E. Ryan, et al., "Matrix Metalloproteinases and Their Inhibition in Periodontal Treatment", *Current Opinion in Periodontology*, 3, 85–96 (1996).

But in this inter-related series of studies it was found that while various modified tetracyclines inhibited the activity of matrix metalloproteinase elastase, the tetracyclines characterized at that time did not inhibit the in vitro serine proteinase elastase activity of either rat PMNs or human synovium. See, e.g., L. Golub et al., "Tetracyclines Inhibit Connective Tissue Breakdown: New Therapeutic Implications For an Old Family of Drugs", *Crit. Rev. Oral Biol. Med.*, 2, 297–322 (1991) at pp 300 and 301.

Metalloproteinases and serine proteinases can work in combination to bring about destruction of most of the elements of the extracellular matrix including interstitial stroma and basement membranes. In this interaction 1) cathepsin G (a serine proteinase) can activate MMP-8; 2) human leukocyte elastase (a serine proteinase) can inactivate the major endogenous tissue inhibitors of matrix metalloproteinases (TIMP's); and 3) MMB-8 and MMP-9 can inactivate $\alpha_1$-Proteinase Inhibitor ($\alpha_1$-PI), the major endogenous inhibitor of human leukocyte elastase. See, S. K. Mallya, et al., "Interaction of Matrix Metalloproteinases With Serine Protease Inhibitors," *Annals of the New York Academy of Science*, 732, 303–314 (1994); and A. R. Rinehart, et al., "Human α-Proteinase Inhibitor Binds to Extracellular Matrix In Vitro", *Am. J Respir. Cell Mol. Biol*, 9, 666–679 (1993). Thus by contributing to protease activation and inactivating the endogenous inhibitors, the two classes of proteinases can skew the protease-antiprotease balance toward pathological tissue degradation. While the enzymes are regulated under normal conditions, a breakdown of the control mechanism can lead to various disease conditions characterized by excess serine proteinase activity.

For example, under conditions of infiltration with large numbers of neutrophils such as may be encountered in respiratory distress syndrome, in which the endogenous levels of $\alpha_1$-PI cannot effectively neutralize human leukocyte elastase levels, the protease-antiprotease balance may become so skewed that protection of the endogenous antielastase will not be sufficient to provide protection from HLE mediated injury.

An exogenous proteinase inhibitor which is capable of fully restoring protease-antiprotease balance has, up until now, not been discovered.

SUMMARY OF THE INVENTION

Accordingly, the invention provides a method for inhibiting the excess activity of serine proteinase in a biological system by administering to the biological system, a serine proteinase inhibiting amount of a hydrophobic tetracycline.

The preferred tetracycline is a 4-de(dimethylamino) tetracycline, e.g., 6-deoxy-5α-hydroxy4-de(dimethylamino) tetracycline, and particularly, 6-demethyl-6-deoxy-4-de (dimethylamino)tetracycline.

In one embodiment, 6-demethyl-6-deoxy4-de (dimethylamino)tetracycline is administered to a mammal in an amount sufficient to inhibit the activity of leukocyte elastase and thus inflammatory destruction related to the activity of leukocyte elastase is reduced. The mammal is preferably human, but other animals are also advantageously treated.

The method of the invention is useful for pharmaceutical as well as cosmetic purposes. The inhibitor has considerable advantages as a therapeutic agent which restores protease-antiprotease balance.

DETAILED DESCRIPTION OF THE INVENTION

In the method of the invention, a hydrophobic tetracycline has an effective serine proteinase elastase inhibitory activity.

Human leukocyte elastase (HLE) and cathepsin G are serine proteinases found in the azurophilic granules of human polymorphonuclear leukocytes (neutrophils). This elastase is sometimes referred to human neutrophil elastase (HNE). The natural substrate, elastin, is a flexible protein that is highly cross-linked by desmosine and α-isodesmosine and other cross-linking moieties. Serine proteinase elastase is capable of degrading elastic fibers, type IV collagen (which occurs in the basement membrane of blood vessels), type III collagen which occurs in gingiva and smooth muscles, proteoglycans, adhesion glycoproteins such as fibronectin and laminin, TIMP's, and other protein components of connective tissue and interstitial fluid.

The serine proteinase human leukocyte elastase (HLE) has the potential for tissue destruction in many disease states such as arthritis, periodontal disease, glomerulonephritis, acute lung disease, cystic fibrosis, and some malignant cancers characterized by invasion of the extracellular matrix by tumor cells. HLE activity has been implicated in septic shock, multiple organ failure (MOF) and myocardial ischemia-reperfusion injury. HLE has also been implicated in the mechanism of lung injury associated with emphysema and adult respiratory distress syndrome (ARDS). The lung damage is believed to be caused, at least in part, by an imbalance between proteases and endogenous antiproteinases (e.g., TIMP and $\alpha_1$-PI). The major endogenous antiproteinase which inhibits leukocyte elastase is $\alpha_1$-PI.

It has now been discovered that a chemically modified tetracycline can be used for leukocyte elastase inhibitory activity. The tetracycline is a hydrophobic 4-de (dimethylamino)tetracycline, most preferably 6-demethyl-6-deoxy-4-de (dimethylamino)tetracycline (CMT-3). Inhibition of HLE will not only reduce the direct tissue injury caused by this enzyme, but will also preserve levels of the TIMPs, thus maintaining the endogenous inhibitors of MMPs in their active state.

The inhibition of neutrophil proteases using non-antibacterial tetracyclines does not place effective response to infection at any appreciable risk because these compounds when employed at doses consistent with their in vitro inhibitory activity, are not likely to impair the capacity of neutrophils to extravasate and invade the interstitial stroma in response to chemoattractants generated at sites of bacterial infection.

Certain CMT's, particularly CMT-3 have now been found to demonstrate substantial leukocyte elastase inhibitory activity while minocycline, doxycycline and other chemically modified tetracyclines do not exhibit substantial leukocyte elastase inhibitory activity.

Figure 1:
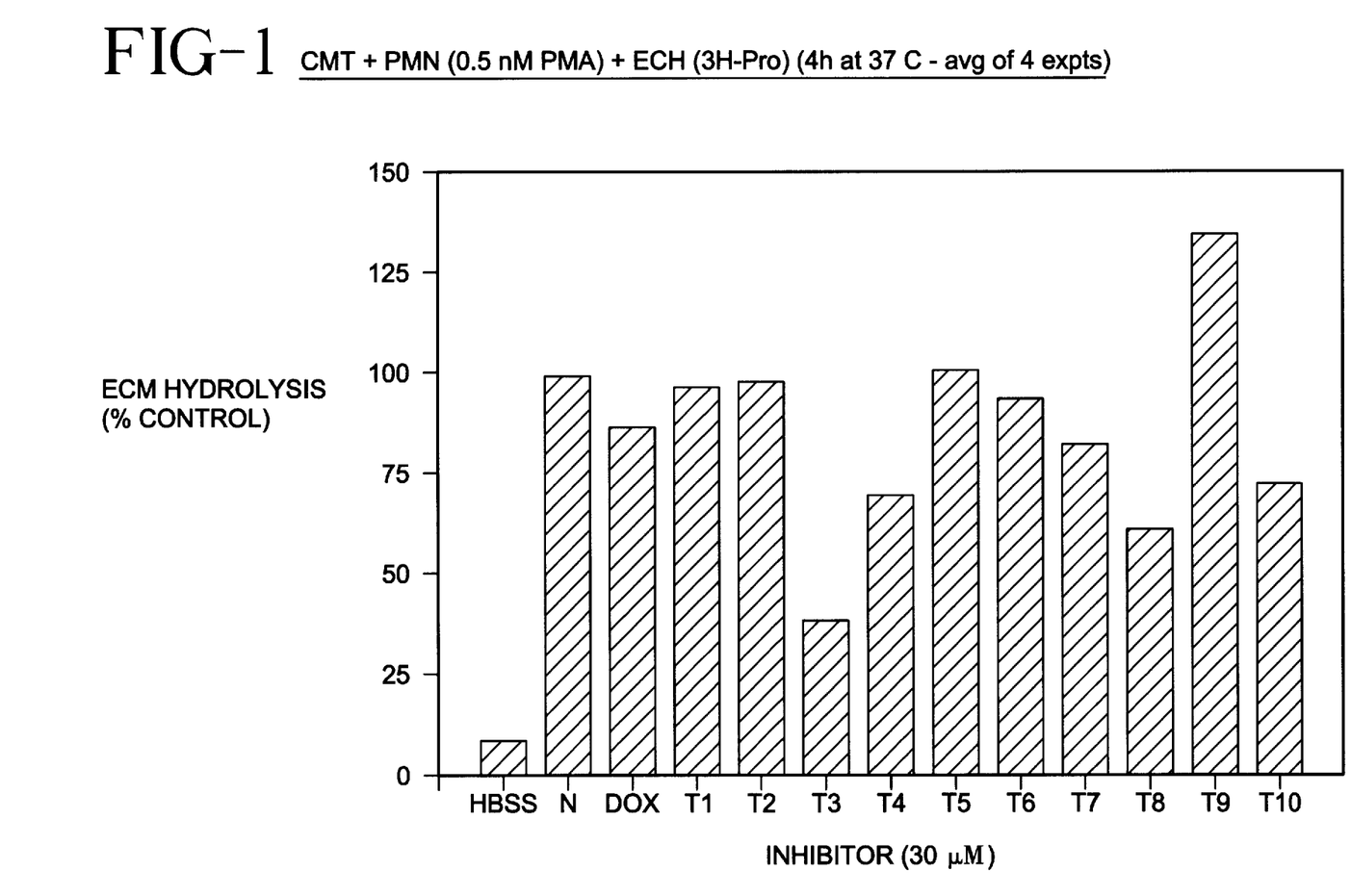
FIG. 1 is a bar graph of the inhibition of human neutrophil-mediated degradation of extracellular matrix by eleven different tetracyclines, as discussed in EXAMPLE 1. A study of the dose dependence of this inhibition is shown in Table I.

The activity of various tetracyclines was investigated employing an in vitro assay of inflammatory tissue injury in which human neutrophils are allowed to degrade a biosynthetically prepared complete interstitial stromal extracellular matrix (ECM). A neutrophil is one type of leukocyte (polymorphonuclear leukocyte). Studies with this experimental system show that neutrophil-mediated degradation of this ECM can be virtually completely inhibited by addition of αhd 1-PI, which is a potent inhibitor of leukocyte elastase as well as a competitive substrate for the MMPs. E. J. Roemer, K. J. Stanton, and S. R. Simon, "In Vitro Assay Systems for Inflammatory Cell-Mediated Damage to Interstitial Extracellular Matrix," In Vitro *Toxicol.* 7,75–81 (1994); E. J. Roemer, K. J. Stanton, and S. R. Simon, "In Vitro Assay Systems for Cell Interactions With Interstitial Extracellular Matrix," In Vitro *Toxicol.* 7,209–224 (1994). When the tetracyclines were tested (Example 1) for their capacity to inhibit ECM degradation in this system, at a dose, for example, of 30 $\mu$M, CMT-3 was far superior to other tetracyclines in protecting the ECM from neutrophil-mediated destruction as shown in FIG. 1. In further dose response studies using this in vitro assay approximately 50% inhibition of neutrophil-mediated ECM degradation can be achieved with 25–50 $\mu$M. Most of the other tetracyclines tested over the same dose range were incapable of inhibiting more than ~20% of neutrophil-mediated ECM degradation using this assay.

Figure 3A:
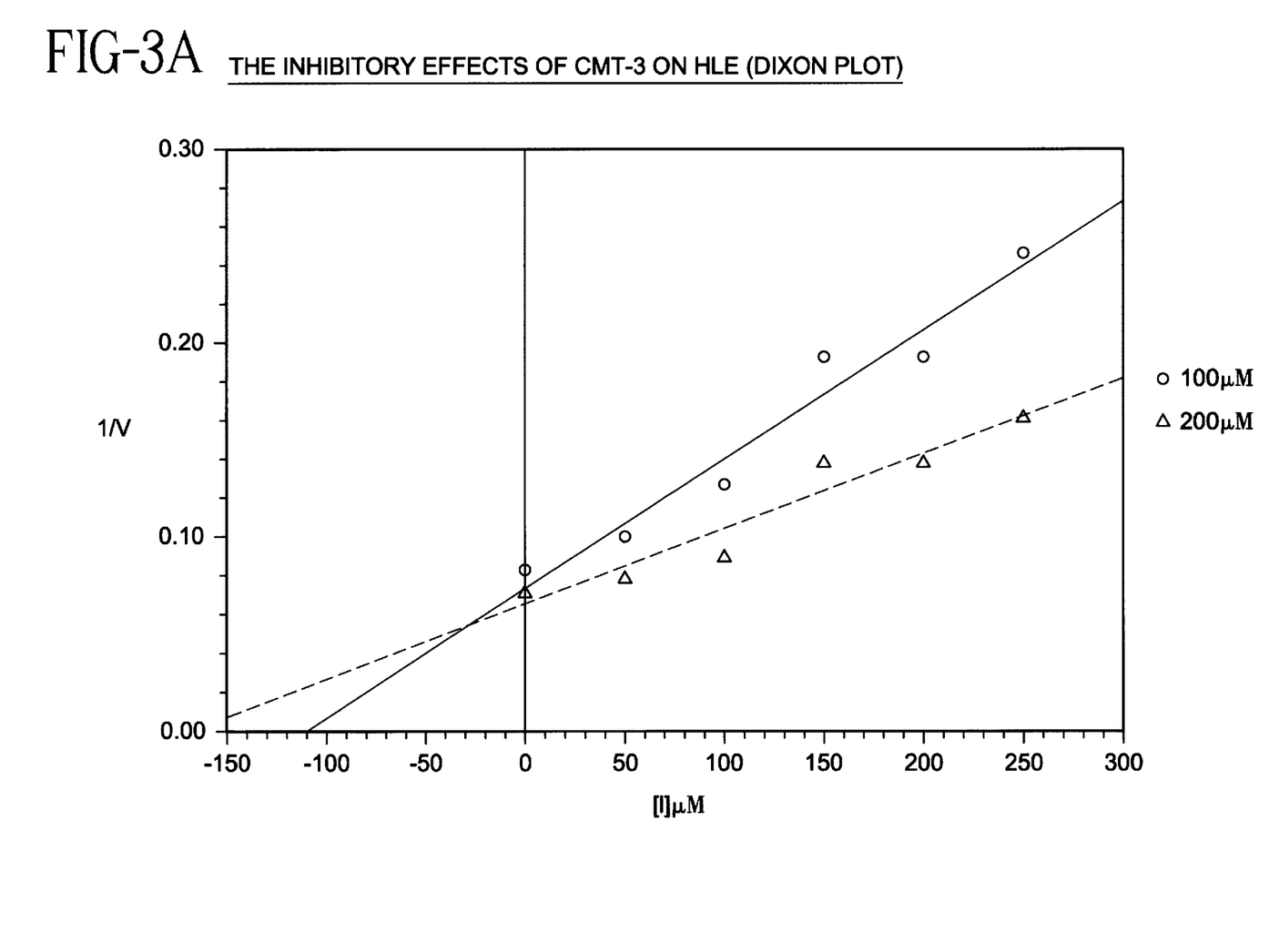
FIGS. 3A,B and 4A,B illustrate Dixon plots (FIGS. 3A and 4A) and Cornish-Bowden plots (FIGS. 3B and 4B) of inhibition of human leukocyte elastase amidolytic activity by CMT-3 (COL-3), as discussed in EXAMPLE 2. The intersection of the Dixon plots above the X-axis and the parallel slopes of the Cornish-Bowden plots confirm that CMT-3 (COL-3) is competitive inhibitor of human leukocyte elastase amidolytic activity towards the oligopeptide chromogenic substrate methoxysuccinyl-Ala-Ala-Pro-Val-p-nitroanilide.
Figure 3B:
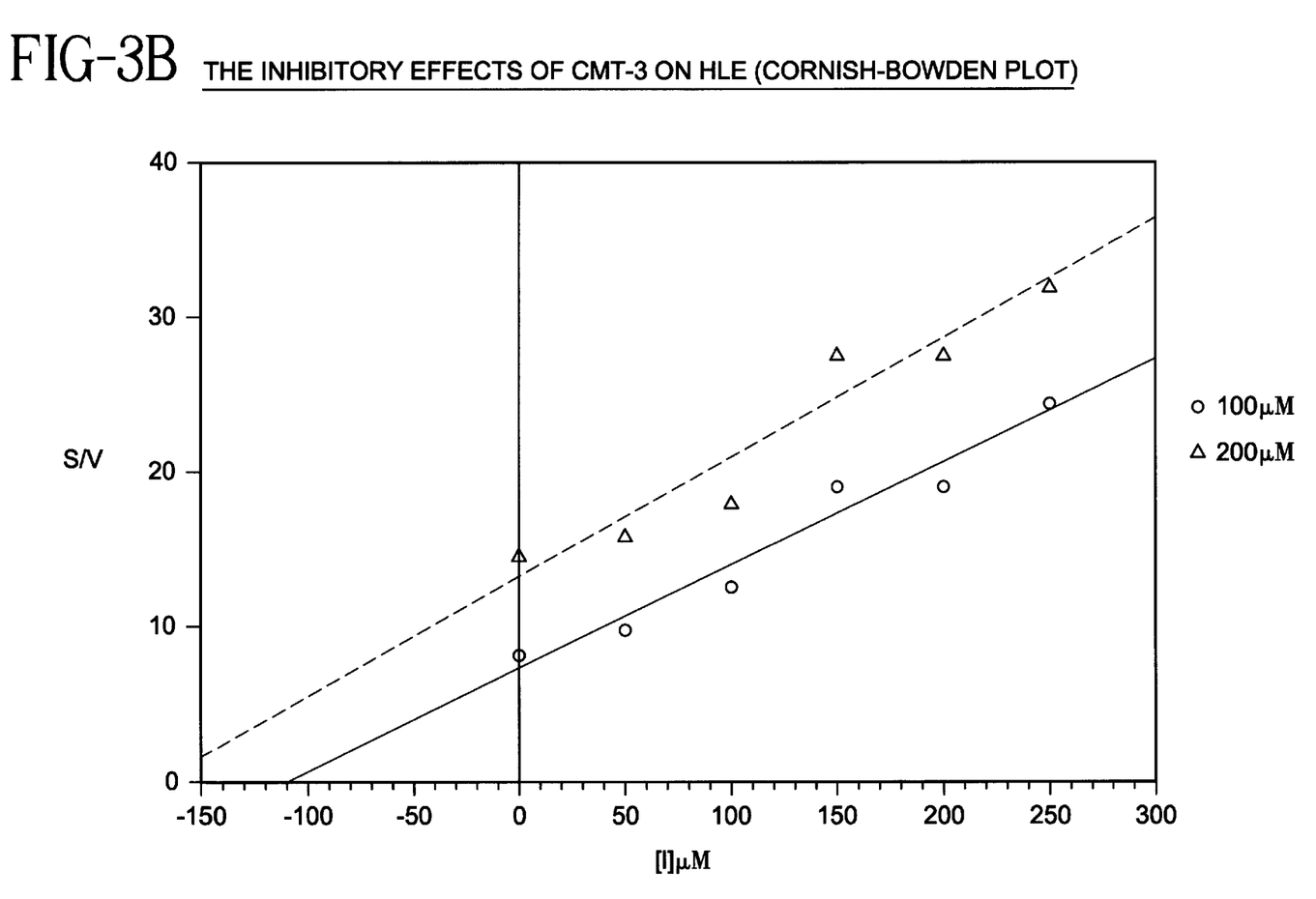
Figure 4A:
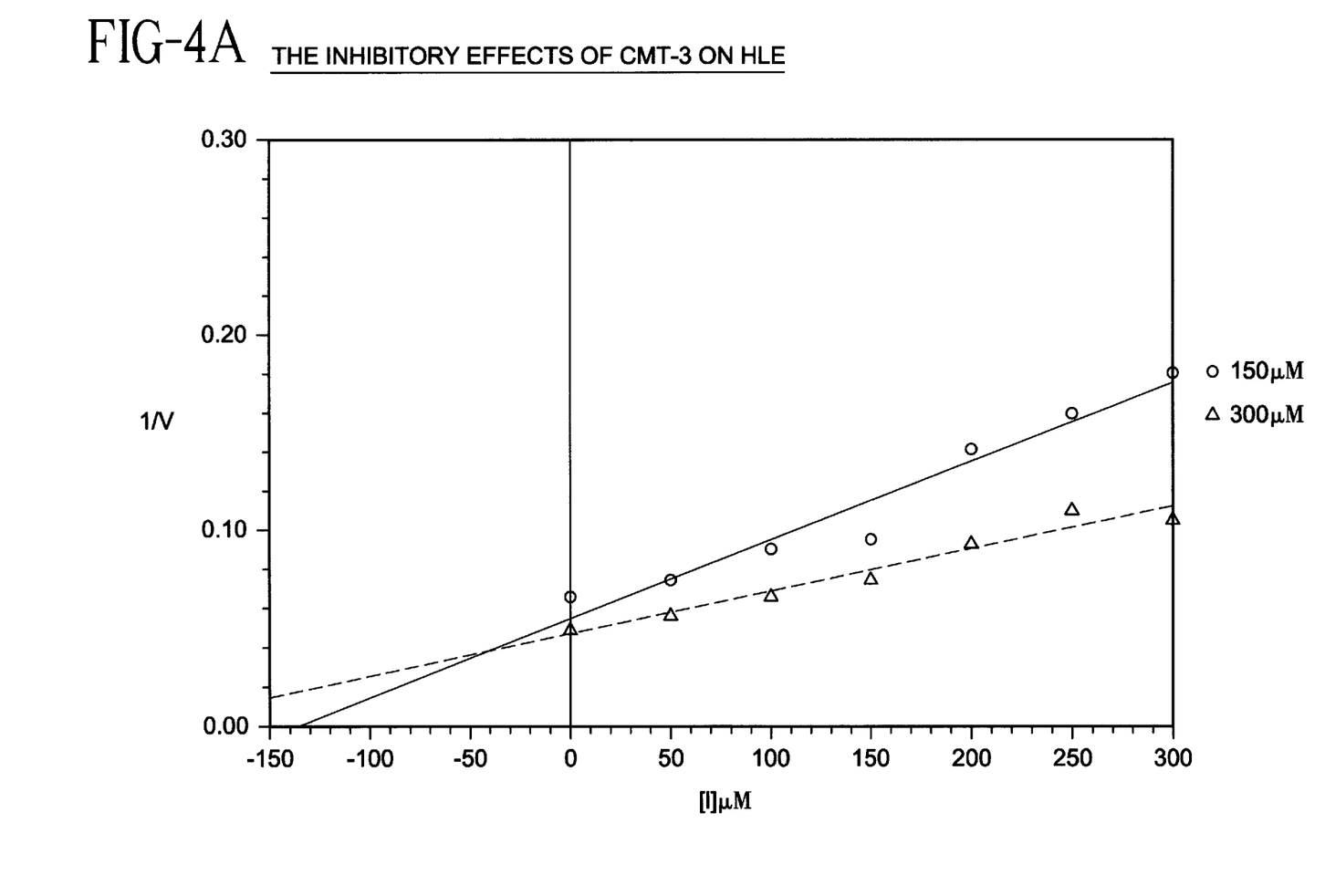
Figure 4B:
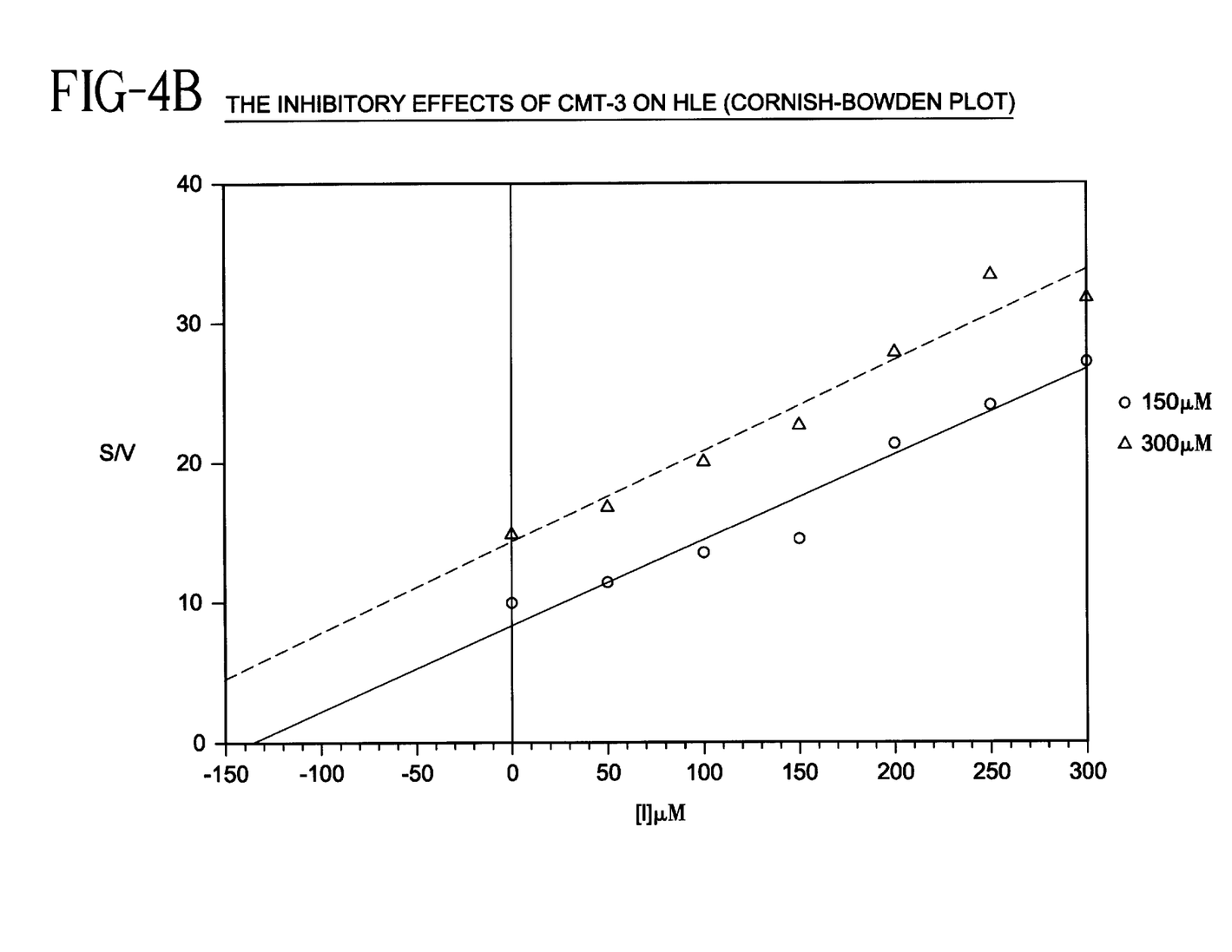

Direct inhibition of HLE by CMT-3 was determined (Example 2) using a modification of the assay of human leukocyte elastase (HLE) activity described by Ying et al. (Q. Ying, A. R. Rinehart, S. R. Simon, and J. C. Cheronis, "Inhibition of Human Leukocyte Elastase by Ursolic Acid:

Evidence for a Hydrophobic Binding Site for Pentacyclic Triterpenes," *Biochem. J.* 277, 521–526 (1991)) in which the organic solvent and detergent concentrations have been reduced, using a traditional assay of human leukocyte elastase (HLE) activity by measurement of the amidolysis of the chromogenic oligopeptide substrate, methoxysuccinyl-Ala-Ala-Pro-Val-p-nitroanilide. This oligopeptide is generally assumed to occupy the first five subsites of the extended substrate binding domain in HLE. Using a combination of Dixon and Cornish-Bowden plots to analyze the rate data in the same fashion as previously described for other nonpeptidic elastase inhibitors by Ying et al. (*Biochem. J.* 277, 521–526 (1991)), we show that CMT-3 is a predominantly competitive inhibitor of the amidolysis of methoxysuccinyl-Ala-Ala-Pro-Val-p-nitroanalide, with an apparent $K_1$ of 18–40 $\mu M$ as illustrated in FIGS. 3A,B and 4A,B. In contrast, doxycycline, which is capable of inhibiting MMP-8 activity in vitro with a $K_1$ of 25–50 $\mu M$, is only a very weak inhibitor of HLE, with a $K_1$ in excess of 300 $\mu M$ as shown by the slope of the Dixon plot in FIG. 5. When CMT-3 is employed in the assay of ECM degradation mediated by purified HLE rather than live neutrophils, it proves to be an effective inhibitor, with an apparent $I_{50}$ of ~25–50 $\mu M$.

In vivo assays (Example 3) demonstrated that administration of CMT-3 to rats in which acute periodontal inflammation was induced by administration of endotoxin reduced the activity of leukocyte elastase, as assayed by an amidolytic assay with the substrate succinyl-Ala-Ala-Ala-p-nitroanilide.

The conditions treatable by means of the present invention occur in mammalian subjects. Human patients are by far the most important subjects, but the method can be practiced for the benefit of other mammals, including, for example, pet animals, such as dogs and cats, and laboratory animals, such as rats and mice, as well as farm animals.

The method of the invention can be used to treat subjects suffering from tissue damage resulting from excess human leukocyte elastase activity, for example, in some lung diseases and renal diseases. The lung diseases of this type include cystic fibrosis, emphysema, adult respiratory distress syndrome as a complication of polytrauma, surgical stress, sepsis, or as a component of multiple organ failure; also acute lung injury resulting from inhalation of toxicants such as acids, chemicals, industrial and military poisons and smoke and other toxic products of combustion. The renal diseases of this type include glomerulonephritis and acute renal failure as a complication of polytrauma or sepsis, or as a component of multiple organ failure.

The method can also be used to treat lesions and inflammatory skin diseases involving marked infiltration of the dermal-epidermal junction with neutrophils and resulting in separation of the dermal-epidermal junction. Such conditions may be of immunologic origin (autoimmune or as a result of drug reactions) or may be triggered by a bacterial toxin (as in "scalded skin" of infants). It is highly likely that leukocyte elastase contributes to the destruction of the dermal-epidermal junction in these conditions. Some lesions triggered by chemical vesicating agents (including both industrial and military exposures) in which neutrophilic infiltration and separation of the dermal-epidermal junction occur also involve leukocyte elastase, and are also candidates for management by CMT-3 therapy. Some lesions of the eye also have neutrophilic infiltration as a component of the injury, and may be managed more effectively with a antiproteinase like CMT-3.

The method of the invention involves the administration of the tetracycline compound in an amount which is effective for reducing or inhibiting undesirable consequences associated with excess leukocyte elastase activity. The preferred tetracycline compound is modified chemically to reduce or eliminate its antimicrobial properties. Such a chemically-modified tetracycline can be used at higher levels than antimicrobial tetracyclines, while avoiding certain disadvantages, such as the indiscriminate killing of beneficial microbes which often accompanies the use of antimicrobial or antibacterial amounts of such compounds.

The maximal dosage for a subject is the highest dosage which does not cause undesirable or intolerable side effects. For example, the tetracycline compound can be administered in an amount of from about 0.1 mg/kg/day to about 24 mg/kg/day, and preferably from about 2 mg/kg/day to about 18 mg/kg/day. For the purpose of the present invention, side effects include clinically significant antimicrobial or antibacterial activity, as well as toxic effects. For example, a dose in excess of about 50 mg/kg/day would likely produce side effects in most mammals, including humans. In any event, the practitioner is guided by skill and knowledge in the field, and the present invention includes without limitation dosages which are effective to achieve the described phenomena.

The preferred pharmaceutical composition for use in the method of the invention comprises a combination of the tetracycline compound in a suitable pharmaceutical vehicle as understood by practitioners in the art.

For the pharmaceutical purposes described above, the tetracycline of the invention can be formulated per se in pharmaceutical preparations optionally with known pharmaceutically acceptable adjuvants or carriers. These preparations can be made according to conventional chemical methods and can be administered internally, e.g., orally by tablet or liquid, or by suppository; parenterally, e.g., intravenously, intramuscularly or subcutaneously, as injectable solutions or suspensions; topically or in the form of a spray or aerosol of droplets within the respirable range for inhalation into the lungs and airways. Such aerosols may include vehicles such as pulmonary surfactant preparations which may contribute additional therapeutic efficacy. Time-release or controlled-delivery administration may be employed.

Pharmaceutical or cosmetic preparations contain a serine proteinase-inhibiting, particularly leukocyte elastase-inhibiting, effective amount of the tetracycline.

In another embodiment, the tetracycline can be used as an agent in cosmetic preparations such as skin creams and lotions, cosmetic masks, cosmetic wraps, cosmetic dressings and shampoos for cosmetic treatments. It shall be understood that the term cosmetic means intended to enhance or improve physical appearance.

For topical or cosmetic application, suitable formulations include, but are not limited to, liposomes, solutions, suspensions, emulsions, creams, ointments, powders, liniments, salves, aerosols, etc., which are, if desired, sterilized and/or mixed with auxiliary agents, e.g., preservatives, stabilizers, wetting agents, buffers, or salts for influencing osmotic pressure, etc.

It will be appreciated that the actual preferred amounts of active compound in a specified case will vary according to the particular compositions formulated, the mode of application, and the particular sites and subject being treated. Dosages will be determined using conventional considerations, e.g., by customary comparison of the differential activities of the formulations and of a known agent, e.g., by means of an appropriate conventional pharmacological or cosmetic protocol.

For cosmetic uses, many additional biocompatible or biologically inert materials may be incorporated with the tetracycline. Biocompatible means non-toxic or non-damaging to human and non-human tissue. These additional materials include, e.g., humectants, i.e., substances having affinity for water such as glycerine, propylene glycol or isopropanolpropylene glycol, organic or inorganic salts such as quaternary ammonium compounds and zinc salts, alcohols such as benzyl alcohol or lower aliphatic alcohols, polymer latices, fillers such as silica and talc, oils such as mineral oil, castor oil and petrolatum, wetting or dispersing agents or surfactants such as block copolymers of ethylene oxide and propylene oxide, dyes, fragrances, pigments, zinc oxide, titanium dioxide, topical medicaments such as methylsalicylate, nicotinates, capsaicin and menthol, anti-acne medicaments such as benzoyl peroxide, resorcinol and retinoic acid, topical antibacterials such as silver sulfadiazine, other tetracyclines and cefazolin, skin hydrating agents such as sodium pyrrolidine carboxylic acid, and UV-A and/or UV-B absorbing sunscreening agents such as p-aminobenzoic acid (PABA) or 2-ethylhexyl 4-N,N-dimethylaminobenzoate (Padimate O). Sustrates can also be used to provide reinforcement, a gas or liquid barrier, or protection of the area of treatment. Substrates are virtually unlimited and include polymer films, metal foils, cellulosics and other natural or synthetic materials.

The following examples are provided to assist in a further understanding of the invention and are not intended to be limiting upon the reasonable scope.

EXAMPLE 1

The serine proteinase inhibiting activity of tetracyclines was tested using an in vitro assay of inflammatory tissue injury in which human neutrophils (live PMN's) were allowed to degrade a biosynthetically prepared complete interstitial stromal extracellular matrix (ECM) produced by cultured R22 rat heart smooth muscle cells as described by Roemer et al. (E. J. Roemer, K. J. Stanton, and S. R. Simon, "In Vitro Assay Systems for Inflammatory Cell-Mediated Damage to Interstitial Extracellular Matrix," In Vitro Toxicol. 7,75–81 (1994); E. J. Roemer, K. J. Stanton, and S. R. Simon, "In Vitro Assay Systems for Cell Interactions With Interstitial Extracellular Matrix," In Vitro Toxicol. 7,209–224 (1994)). Ten different chemically modified tetracyclines (CMTs) designated CMT-1 through CMT-10 and doxycycline, at concentrations ranging from 5 $\mu$M to 50 $\mu$M, were added to the ECM simultaneously with a suspension of $2\times10^6$ viable human PMN/mL in Hank's balanced salts solution (HBSS). In these studies, the ECM was metabolically radiolabeled with $^3$H-proline, and counts solubilized after six hours of incubation were measured and compared with counts released after incubation with PMN alone. The results for concentrations of 5 $\mu$m, 25 $\mu$m and 50 $\mu$m are shown in Table 1 and and the results for 30 $\mu$m are shown in FIG. 1.

TABLE 1

EFFECT OF CMTs ON PMN (+0.5 nM PMA)-
MEDIATED R22-ECM HYDROLYSIS
(3H-Pro cpm released in 6h at 37° C.)
ASSAY
ECM HYDROLYSIS (% CONTROL)

|  | 5 $\mu$m | 25 $\mu$m | 50 $\mu$m |
| --- | --- | --- | --- |
| DOXYCYCLINE | 98 | 92 | 84 |
| CMT-1 | 93 | 95 | 90 |
| CMT-2 | 91 | 95 | 100 |
| CMT-3 | 69 | 55 | 50 |
| CMT-4 | 90 | 98 | 130 |
| CMT-5 | 78 | 112 | 102 |
| CMT-6 | 109 | 101 | 97 |
| CMT-7 | 97 | 84 | 100 |
| CMT-8 | 96 | 82 | 57 |
| CMT-9 | 88 | 215 | 190 |
| CMT-10 | 101 | 85 | 80 |

Note: The ECM hydrolysis is expressed as % control where the control is hydrolysis in absence of any inhibitor normalized to 100%

Table 1 and FIG. 1 show that CMT-3 was capable of achieving significant inhibition of neutrophil-mediated ECM degradation (~50% inhibition at concentrations $\geq$25–30 $\mu$M) and with good inhibition of ECM degradation at all doses employed in this assay. CMT-8 and CMT-10, particularly CMT-8, at some concentrations, showed some inhibition of ECM degradation.

Figure 2:
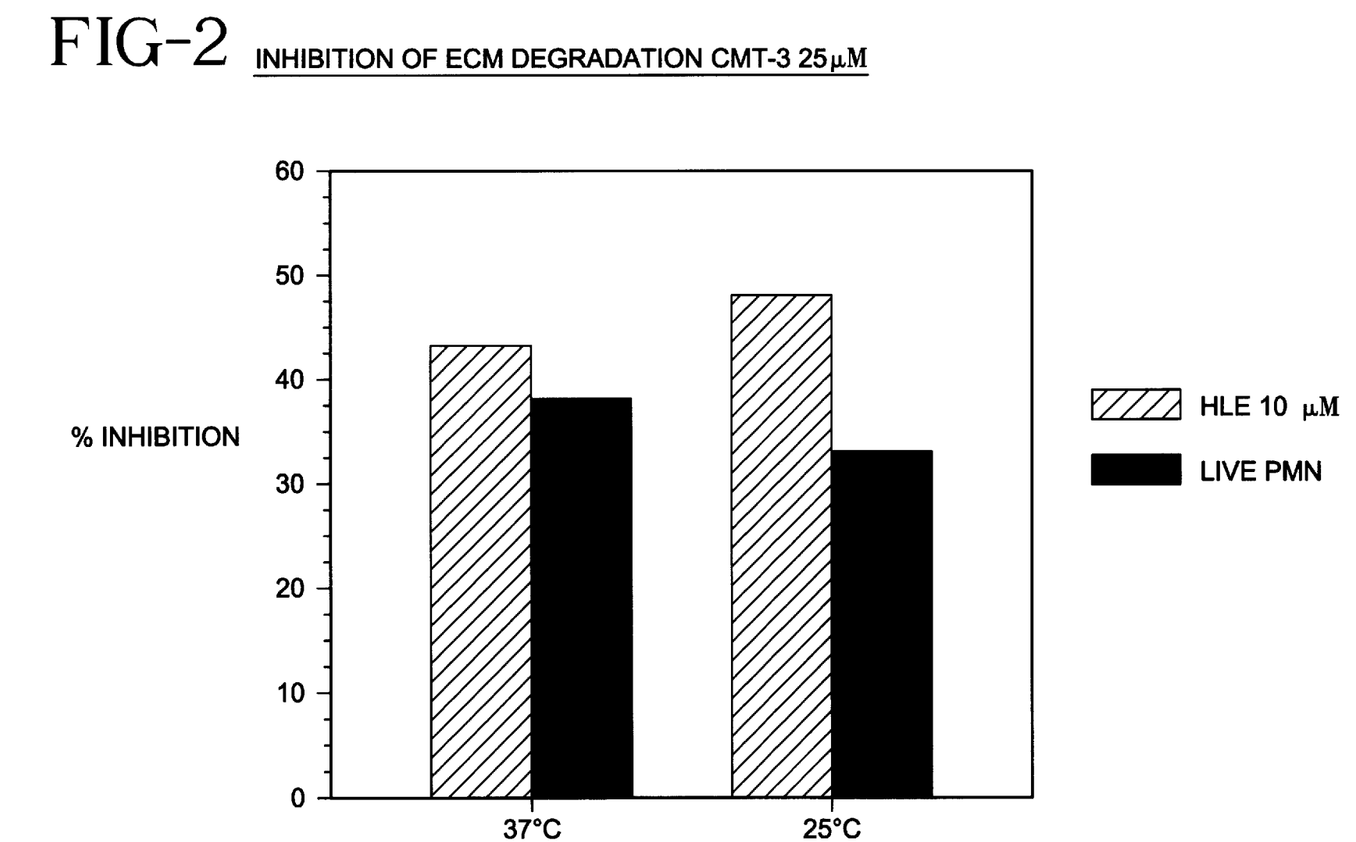
FIG. 2 is a bar graph illustrating comparable inhibition of human neutrophil-mediated and human leukocyte elastase-mediated degradation of extracellular matrix by CMT-3 (COL-3), as discussed in EXAMPLES 1 and 2.

FIG. 2 illustrates a comparison of the inhibitory potency of 25 $\mu$M CMT-3 (COL-3) in parallel assays of ECM degradation mediated either by $2\times10^6$ PMN/mL or by 10 $\mu$M purified HLE, using the same methods as cited above.

EXAMPLE 2

The direct inhibitory effect of tetracyclines on the amidolytic activity of human leukocyte elastase (HLE) was evaluated by the method described by Ying et al., Biochem. J. 277, 521–526 (1991), modified by lowering the DMSO concentration to 2% and eliminating the use of the detergent Triton X-100. To avoid time-dependent adsorption of HLE onto the wells of the 96-well microplates used in the amidolytic assays, the plates were pretreated with a solution of 0.2% bovine serum albumin. A range of concentrations of the chromogenic oligopeptide substrate methoxysuccinyl-Ala-Ala-Pro-Val-p-nitroanilide from 100 $\mu$M through 300 $\mu$M was employed for all measurements; this substrate is believed to occupy substrate binding subsites $S_1$ through $S_5$, in HLE on the basis of X-ray crystallographic analysis (W. Bode, E. Meyer, and J. C. Powers, "Human Leukocyte and Porcine Pancreatic Elastase: X-Ray Crystal Structures, Mechanism, Substrate Specificity, and Mechanism-Based Inhibitors," Biochemistry 28, 1951–1963 (1989)). Inhibition of amidolytic activity was analyzed by the graphical methods of Dixon (M. Dixon, Biochem. J. 55, 170–171 (1953)) and Cornish-Bowden (A. Cornish-Bowden, Biochem. J. 137, 143–144 (1974)) as in Ying et al.: intersection of Dixon plots obtained at different substrate concentrations at a point above the X-axis rules out a mechanism of pure noncompetitive inhibition, while parallel Cornish-Bowden plots obtained at different substrate concentrations are consistent with pure competitive inhibition. The substrate concentration at which the Dixon plots intersect is a measure of $K_i$ for the inhibitor. Typical Dixon and Cornish-Bowden plots for inhibition of HLE by CMT-3 (COL-3) are illustrated in FIGS. 3A,B and 4A,B. From these data, the $K_i$ for inhibition of amidolytic activity of HLE by CMT-3 can be estimated to be 25–40 $\mu$M. In the presence of 10% dimethylsulfoxide and 0.1% Triton X-100, the inhibitory potency of CMT-3 is markedly reduced, supporting the conclusion that hydrophobic interactions contribute to stabilization of binding of CMT-3 to HLE.

Figure 5:
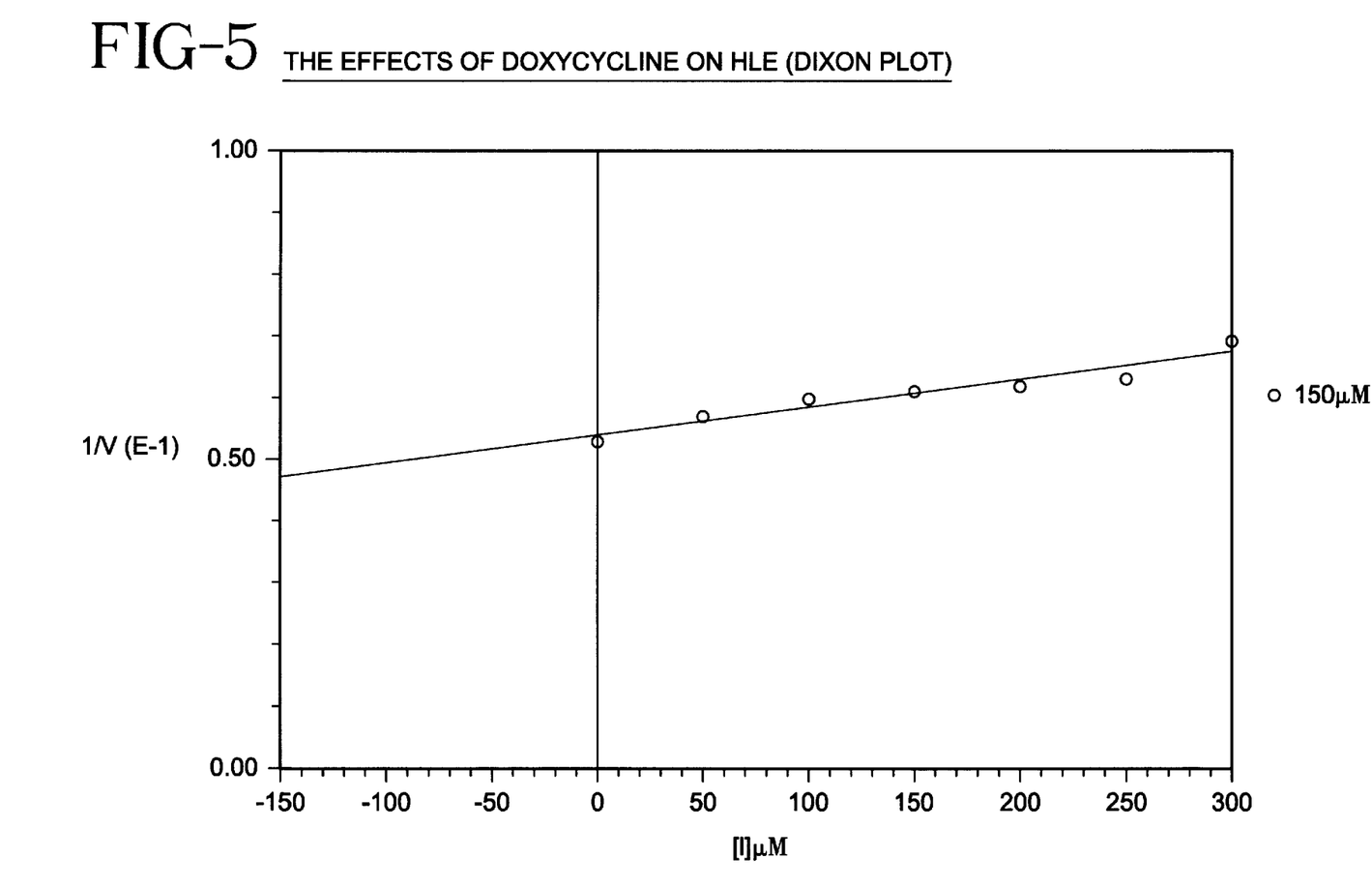
FIG. 5 illustrates a Dixon plot of HLE amidolytic activity in the presence of doxycycline, showing only very weak inhibition by this tetracycline in contrast to CMT-3, as discussed in EXAMPLE 2.

The inhibitory activity of doxycycline towards amidolysis of methoxysuccinyl-Ala-Ala-Pro-Val-p-nitroanilide by HLE was also determined in the presence of 2% DMSO and no detergent, as described above for CMT-3. Analysis of the slope of the Dixon plot for inhibition of amidolytic activity of HLE by doxycycline indicates a much higher value of $K_i$, around 300 μM, as illustrated in FIG. 5. Other tetracycline derivatives which showed comparably low or no potency as inhibitors of the amidolytic activity of HLE were oxytetracycline and its 4-epimer, epi-oxytetracycline; chlorotetracycline and its 4-epimer, epi-chlorotetracycline; anhydrochlorotetracycline; and CMT-5, a chemically modified tetracycline in which the oxo and hydroxy moieties at the base of the four fused rings are replaced by a pyrazole ring. It is believed that because it uniquely lacks any substituents on either the 6- or the 4-positions of the fused ring system of the tetracyclines, CMT-3 unexpectedly appears to be capable of binding with much greater affinity to HLE than any of the other tetracyclines tested.

The capacity of CMT-3 to inhibit HLE is not confined to amidolytic assays, as already shown in FIG. 2, in which the degradation of a complete interstitial extracellular matrix by purified HLE is inhibited by CMT-3. The potency of inhibitory activity of CMT-3 in this assay of inhibition of matrix degradation by HLE is comparable to that determined from the assays of HLE amidolytic activity, consistent with the interpretation that the mechanism of inhibition in both types of assays involves binding of CMT-3 to the enzyme in a fashion which blocks binding of either peptide or protein substrates. In the assay of HLE-mediated degradation of ECM, the other tetracyclines tested were not effective at doses comparable to those tested with CMT-3.

EXAMPLE 3

Figure 6:
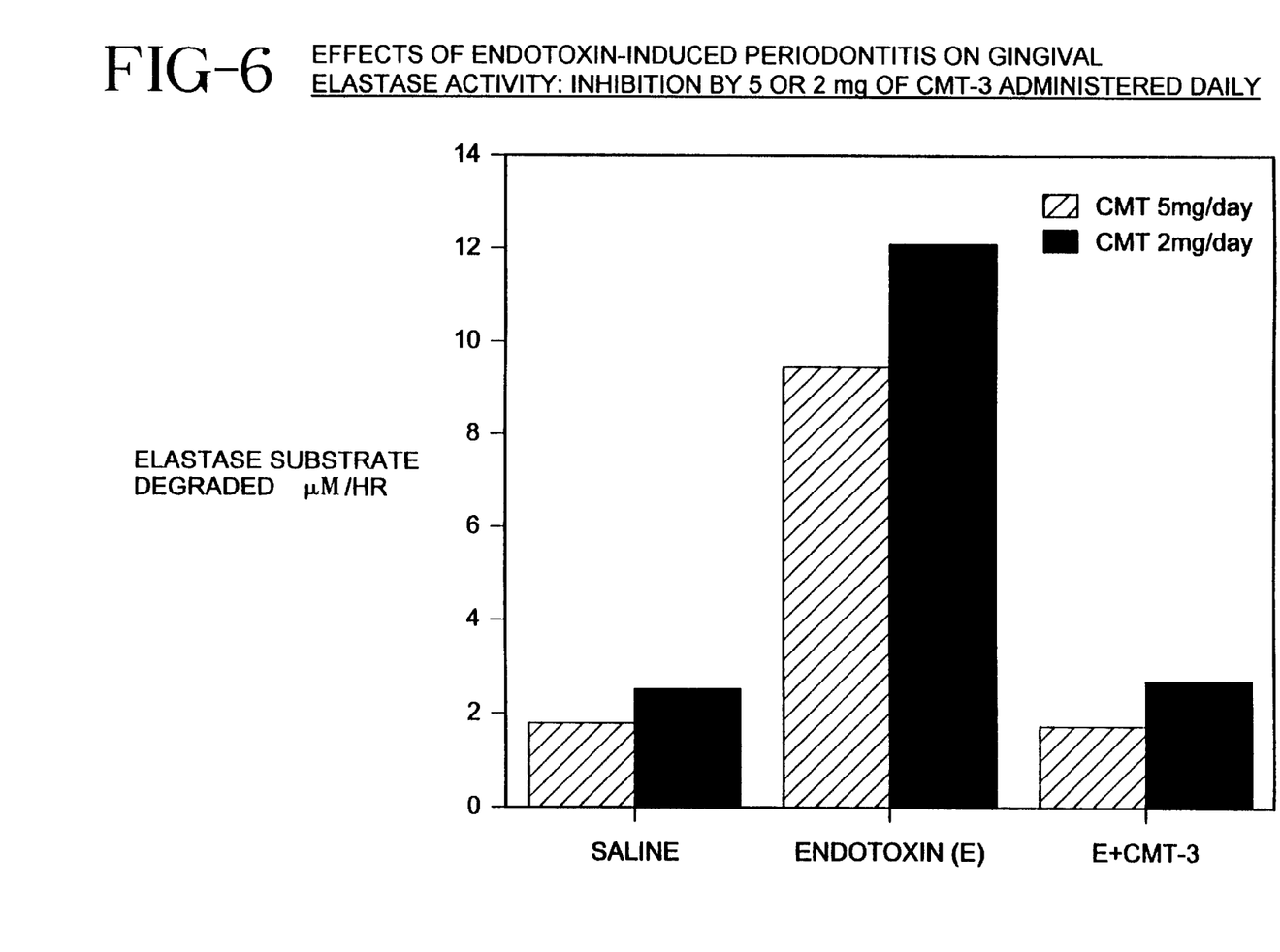
FIG. 6 is a bar graph illustrating the capacity of orally administered CMT-3 to reduce leukocyte elastase activity in gingival tissue extracts of rats which had received gingival injections of bacterial lipopolysaccharide to induce local inflammation in EXAMPLE 3.

The capacity of orally administered CMT-3 (COL-3) to reduce leukocyte elastase activity in vivo in an animal model of acute inflammation and neutrophilic infiltration was demonstrated, using an experimental protocol similar to that described by Chang et al. (K. M. Chang, M. E. Ryan, L. M. Golub, N. S. Ramamurthy, and T. F. McNamara, "Local and Systemic Factors in Periodontal Disease Increase Matrix-Degrading Enzyme Activities in Rat Gingiva: Effect of Minocycline Therapy," Res. Comm. Mol. Path. Pharm. 91, 303–318 (1996)). Rats received 0.01 mg of E. coli lipopolysaccharide (LPS) or only a vehicle of saline injected in a volume of 10 μl into the maxillary and mandibular labial gingiva on alternate days for a period of six days. Two sets of rats also received 2 mg or 5 mg CMT-3 daily in a volume of 1 ml, administered by oral gavage, for the six day period, while the other sets of rats received only the vehicle of 2% carboxymethylcellulose. At the end of the six day treatment period, the animals were sacrificed and the gingival tissues were dissected. The tissues from each experimental group were pooled, frozen and thawed, and extracted for assays of enzymatic activity according to the procedure of Yu et al. (Z. Yu, N. S. Ramamurthy, M. Leung, K. M. Chang, T. F. McNamara, and L. M. Golub, "Chemically Modified Tetracycline Normalizes Collagen Metabolism in Diabetic Rats," J. Periodont. Res. 28, 420–428 (1993)). Leukocyte elastase activity was assayed using the substrate succinyl-Ala-Ala-Ala-p-nitroanilide according to the procedure of Ramamurthy and Golub (1983) (N. S. Ramamurthy, and L. M. Golub, "Diabetes Increases Collagenase Activity in Extracts of Rat Gingiva and Skin," J. Periodont. Res. 18, 23–30 (1983)). The finding reported here is the capacity of orally administered CMT-3 to reduce the level of leukocyte elastase activity in the gingival extracts of LPS-injected rats. FIG. 6 illustrates the reduced levels of leukocyte elastase activity in the gingival extracts of LPS-injected rats treated with both doses of CMT-3, as compared with elastase activity in gingival extracts from rats receiving LPS injections and gavage of vehicle alone or injections of saline. Administration of CMT-3 appears to reduce the levels of elastase activity in the gingival extracts LPS-injected rats to the levels detected in animals receiving gingival injections of saline solution alone. This result demonstrates that CMT-3 administration in vivo can result in reduced leukocyte elastase levels at sites of localized acute inflammation with neutrophil infiltration.

Thus, while there have been described what are presently believed to be the preferred embodiments of the invention, those skilled in the art will realize that changes and modifications may be made thereto without departing from the spirit of the invention, and it is intended to claim all such changes and modifications as fall within the true scope of the invention.

What is claimed is:

1. A method of inhibiting excess leukocyte elastase activity in a biological system comprises administering, to a biological system subject to excess leukocyte elastase activity, a leukocyte elastase activity inhibitory amount of hydrophobic tetracycline.

2. The method of claim 1 wherein the tetracycline is a 4-de(dimethylamino) tetracycline.

3. The method of claim 1 wherein the biological system is mammalian.

4. The method of claim 1 wherein the tetracycline comprises 6-demethyl-6-deoxy-4-de(dimethylamino) tetracycline, 6-deoxy-5α-hydroxy-4-de(dimethylamino) tetracycline, 4-de(dimethylamino)minocycline, or combination thereof.

5. The method of claim 1 wherein the tetracycline comprises 6-demethyl-6-deoxy4-de(dimethylamino) tetracycline.

6. The method of claim 1 wherein the tetracycline further comprises a cosmetic preparation.

7. The method of claim 1 wherein the tetracycline further comprises a pharmaceutical preparation.

8. A method of treating a subject suffering from tissue damage resulting from excess leukocyte elastase activity comprises administering to the subject a leukocyte elastase inhibiting amount of hydrophobic tetracycline.

9. The method of claim 8 wherein the tetracycline is a 4-de(dimethylamino) tetracycline.

10. The method of claim 8 wherein the subject is a mammal.

11. The method of claim 8 wherein the tetracycline comprises 6-demethyl-6-deoxy-4-de(dimethylamino) tetracycline, 6-deoxy-5α-hydroxy-4-de(dimethylamino) tetracycline, 4-de(dimethylamino)minocycline, or combination thereof.

12. The method of claim 8 wherein the tetracycline comprises 6-demethyl-6-deoxy-4-de(dimethylamino) tetracycline.

13. The method of claim 8 wherein the tissue damage resulting from excess leukocyte elastase activity is lung disease.

14. The method of claim 13 wherein the lung disease is cystic fibrosis, emphysema, adult respiratory distress syndrome or acute lung injury resulting from inhalation of toxicants.

15. The method of claim 14 wherein the respiratory distress syndrome is a complication of polytrauma, surgical stress, sepsis or is a component of multiple organ failure.

16. The method of claim 14 wherein the toxicant is an acid, a chemical, industrial poison, military poison, smoke or toxic product of combustion.

17. The method of claim 8 wherein the tissue damage resulting from excess leukocyte elastase activity is renal disease.

18. The method of claim 17 wherein the renal disease is glomerulonephritis, acute renal failure as a complication of polytrauma or sepsis, or acute renal failure as a component of multiple organ failure.

* * * * *

UNITED STATES PATENT AND TRADEMARK OFFICE
CERTIFICATE OF CORRECTION

PATENT NO. : 5,773,430

DATED : June 30, 1998

INVENTOR(S) : Simon, et al

It is certified that error appears in the above-identified patent and that said Letters Patent is hereby corrected as shown below:

Column 2, line 38, please delete "Polyanoinic" and substitute --Polyanionic--.

Column 12, line 28, please delete "subject" and substitute --susceptible--.

Signed and Sealed this

Ninth Day of February, 1999

Attest:

Attesting Officer

*Acting Commissioner of Patents and Trademarks*